US010874480B2

(12) United States Patent
Mangelberger et al.

(10) Patent No.: US 10,874,480 B2
(45) Date of Patent: Dec. 29, 2020

(54) COUPLING DEVICE FOR DETACHABLY CONNECTING A MEDICAL OR DENTAL INSTRUMENT TO A DRIVE UNIT OR A SUPPLY HOSE

(71) Applicant: W&H Dentalwerk Bürmoos GmbH, Bürmoos (AT)

(72) Inventors: Michael Mangelberger, St. Georgen (AT); Christof Baier, Bürmoos (AT); Wolfgang Tannebaum, Weiden (DE)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 154 days.

(21) Appl. No.: 16/058,968

(22) Filed: Aug. 8, 2018

(65) Prior Publication Data

US 2018/0353261 A1 Dec. 13, 2018

Related U.S. Application Data

(63) Continuation of application No. 14/228,028, filed on Mar. 27, 2014, now abandoned, which is a
(Continued)

(30) Foreign Application Priority Data

Oct. 10, 2011 (EP) ........................................ 1184479
Dec. 16, 2011 (EP) ........................................ 1193945

(51) Int. Cl.
*A61B 90/90* (2016.01)
*A61B 90/98* (2016.01)
(Continued)

(52) U.S. Cl.
CPC ............ *A61C 1/0015* (2013.01); *A61B 17/00* (2013.01); *A61B 90/90* (2016.02); *A61B 90/98* (2016.02);
(Continued)

(58) Field of Classification Search
CPC ........... A61C 1/05; A61C 1/08; A61C 1/0015; A61C 1/18; A61C 1/052; A61C 1/088;
(Continued)

(56) References Cited

U.S. PATENT DOCUMENTS 4,720,266 A * 1/1988 Leonard ................... A61C 1/18
433/126
10,485,405 B2 * 11/2019 Mangelberger .......... A61C 1/18
(Continued)

FOREIGN PATENT DOCUMENTS

DE 102009008698 8/2010
EP 1392193 12/2009
(Continued)

*Primary Examiner* — Jacqueline T Johanas
*Assistant Examiner* — Matthew P Saunders
(74) *Attorney, Agent, or Firm* — Klarquist Sparkman, LLP

(57) ABSTRACT

A coupling device for detachably connecting a medical or dental instrument to a drive unit or a supply hose for transfer of at least one of data, energy, a driving movement and a working medium between the drive unit or the supply hose and the instrument includes a first coupling element and a second coupling element. One of the coupling elements includes a coupling recess and the other includes a coupling protrusion insertable therein. One of the coupling elements includes a positioning element and the other includes an indentation into which the positioning element can be inserted to position the coupling elements in a defined angular position about a shared axis. One of the coupling elements includes a memory unit for storage of data and the other includes a transfer unit, so that data can be transferred from the memory unit by the transfer unit to the other coupling element.

23 Claims, 3 Drawing Sheets

Related U.S. Application Data continuation of application No. PCT/EP2012/069907, filed on Oct. 9, 2012.

(51) Int. Cl.
*A61C 19/00* (2006.01)
*A61B 17/00* (2006.01)
*G06K 19/07* (2006.01)
*A61C 1/00* (2006.01)

(52) U.S. Cl.
CPC ............ *A61C 1/0061* (2013.01); *A61C 19/00* (2013.01); *G06K 19/0723* (2013.01); *A61B 2017/00017* (2013.01); *A61B 2017/00411* (2013.01); *A61B 2017/00473* (2013.01); *A61B 2017/00477* (2013.01); *A61B 2017/00482* (2013.01); *A61B 2017/00535* (2013.01); *A61C 2204/005* (2013.01); *Y10T 29/49826* (2015.01)

(58) Field of Classification Search
CPC ....... A61C 1/00; A61C 1/0061; A61C 1/0046; A61B 2017/00482; A61B 90/90; A61B 90/98; G06K 19/0723
USPC .......................................................... 433/126
See application file for complete search history.

(56) References Cited

U.S. PATENT DOCUMENTS

| | | | |
|---|---|---|---|
| 2002/0129454 A1* | 9/2002 | Hilscher | A61C 17/221 15/22.1 |
| 2003/0101526 A1* | 6/2003 | Hilscher | A61C 17/22 15/22.1 |
| 2004/0166464 A1* | 8/2004 | Schneider | A61C 19/004 433/29 |
| 2004/0209223 A1 | 10/2004 | Beier et al. | |
| 2006/0142744 A1 | 6/2006 | Boutoussov | |
| 2010/0221676 A1* | 9/2010 | Kuhn | A61C 1/088 433/29 |
| 2011/0033823 A1* | 2/2011 | Gersh | A61C 17/20 433/119 |
| 2011/0207353 A1* | 8/2011 | Sauter | A61B 17/1626 439/191 |
| 2011/0208206 A1* | 8/2011 | Diamant | A61B 17/2202 606/128 |
| 2012/0129124 A1* | 5/2012 | Lancieux | A61C 1/088 433/29 |
| 2014/0212833 A1* | 7/2014 | Mangelberger | A61B 90/98 433/80 |
| 2014/0363784 A1 | 12/2014 | Monty et al. | |

FOREIGN PATENT DOCUMENTS

| | | |
|---|---|---|
| EP | 2327370 | 6/2011 |
| EP | 2359756 | 8/2011 |

\* cited by examiner

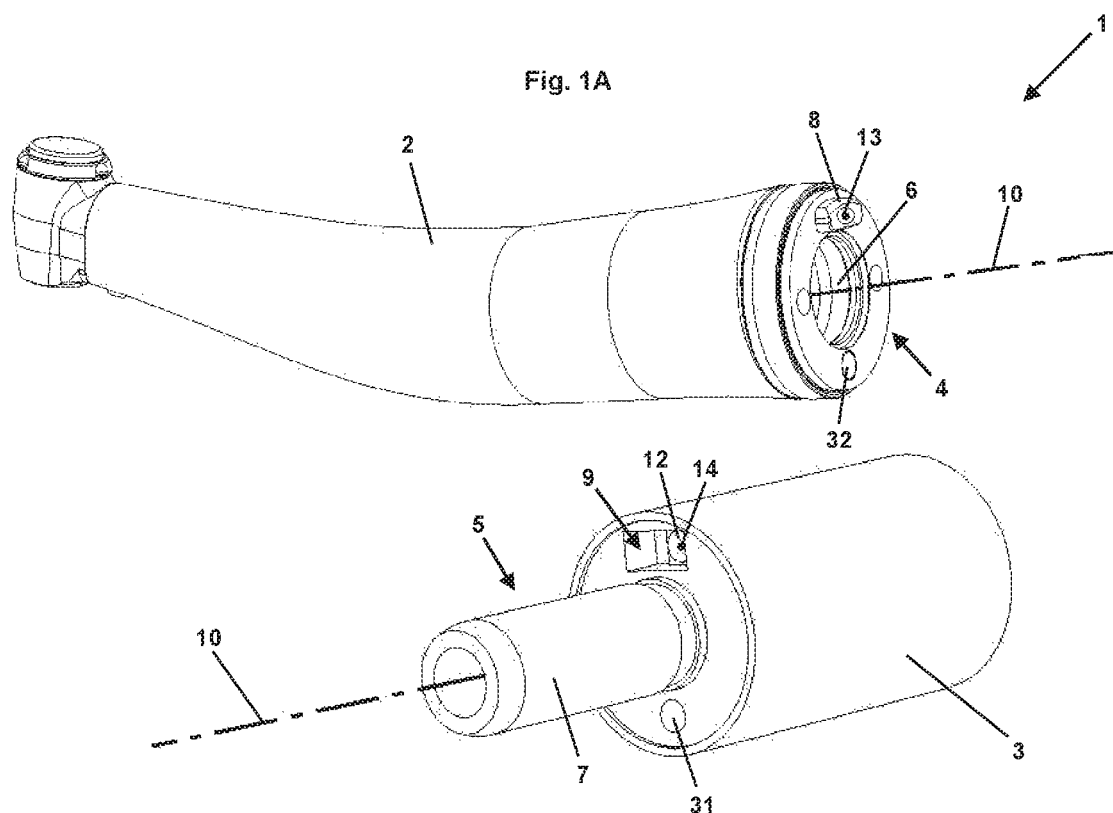
Fig. 1A
Fig. 1B
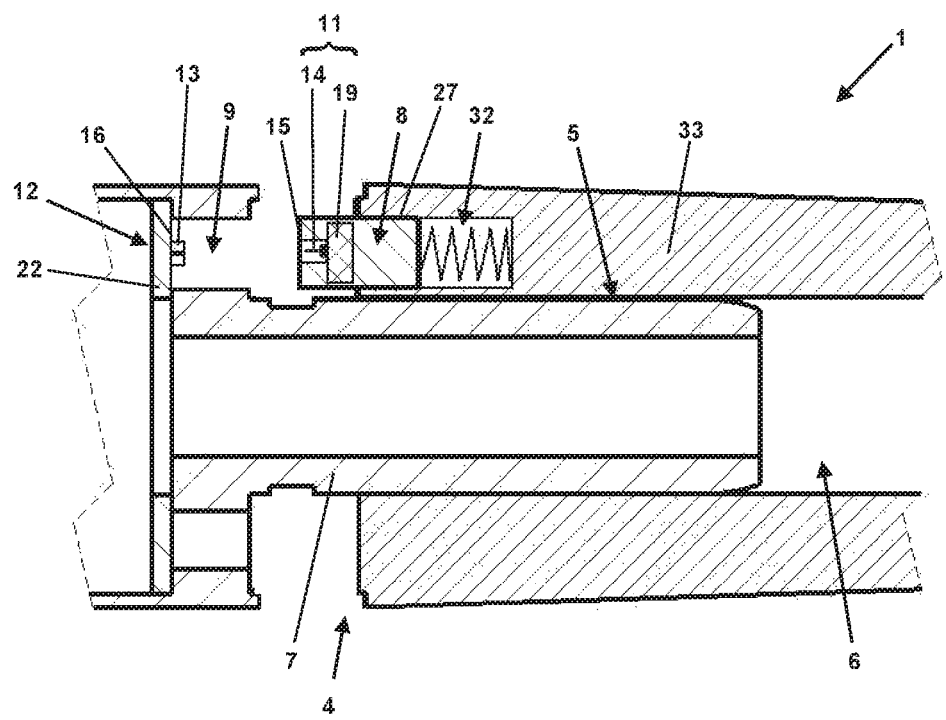
Fig. 2

COUPLING DEVICE FOR DETACHABLY CONNECTING A MEDICAL OR DENTAL INSTRUMENT TO A DRIVE UNIT OR A SUPPLY HOSE

CROSS REFERENCE TO RELATED APPLICATION

This application is a continuation of U.S. patent application Ser. No. 14/228,028, filed Mar. 27, 2014, which is a U.S. bypass continuation application of international application PCT/EP2012/069907, filed on Oct. 9, 2012, which in turn claims priority from European Patent Applications No. EP11193945.0, filed Dec. 12, 2011, and EP11184479.1, filed Oct. 10, 2011, now abandoned. The prior applications are incorporated herein by reference.

BACKGROUND

Field

The present invention relates to a coupling device for detachably connecting a medical, in particular dental, instrument to a drive unit or a supply hose.

Description of Prior Art

Such coupling devices are used for transferring data, energy, light, a drive motion and/or a working medium, in particular a fluid, between two medical, in particular dental, devices. One of the devices here is preferably designed as a medical instrument, in particular as a dental handpiece or angle piece for connection of medical, in particular dental, tools, which are preferably used for working on hard or soft tissue or for introducing implants. In addition, the term instruments is understood in particular to include straight, curved or pistol-shaped handpieces as well as parts of handpieces, adapters and light probes. The handpieces or angle pieces are preferably connected by means of the coupling device, in particular by means of a first coupling element of the coupling device, to the second coupling element, which is preferably disposed on a medical, in particular dental, drive unit or a supply hose in order to drive the medical tools by means of an electric motor disposed in the drive unit. During operation of the medical tools, they as well as the handpieces or angle pieces, are to be supplied with working media, for example, spray air and/or spray water for cooling or for electrical energy. These media are supplied in particular by a dental unit and are supplied to the drive unit or to the handpiece or angle piece by means of a supply line by way of the coupling device.

These instruments often have a code for identification, in particular the handpieces and angle pieces, to supply the working media automatically as a function of the instrument connected to the unit by the supply hose. This code, which contains in particular identification data, for example, a serial number, is usually read out by an electronic unit of the dental unit to thereby select the respective operating parameters for the working media from a memory unit in the dental unit for operation of the instrument connected to the unit.

Furthermore, it is known that in addition to the identification data, the operating parameters for operation of the instrument may be stored in the medical instrument, in particular in a data memory disposed therein. The electronic system of the dental unit recognizes the instrument based on the identification data and at the same time adjusts the parameters for the working media on the dental unit based on the operating parameter data stored in the memory of the instrument. The operating parameter data of the instruments refer in particular to torques, rotational speeds, transmission ratios and efficiencies.

It is also known that the data memory may be designed to be writable and/or rewritable. In addition to the identification and operating parameter data, which are stored in the memory, additional data, in particular service and maintenance data, for example, running times, service work, care and/or cleaning data may be written to the memory and/or compiled there.

A medical instrument having such a coupling device with a first and a second coupling element for supplying the instrument with media as well as having a memory in the interior of the medical instrument is known from the patent EP 1 392 193 B1.

This known instrument comprises an outer sleeve in which a coupling recess of a first coupling element is provided for input of a coupling pin of a second coupling element of a coupling device for supplying the instrument with media, in particular with water, compressed air or light. A working shaft, which can be connected to a driveshaft of the other coupling element, is disposed in the recess, so that the working shaft of the instrument can preferably be induced to a rotational movement. A memory element for identification data and/or operating parameter data is provided in the interior of the medical instrument. This memory element is disposed in the sleeve wall surrounding the coupling recess and is accessible for the corresponding coupling element from the inside lateral surface of the sleeve wall or from the rear annular end face of the sleeve wall. In another exemplary embodiment, the memory element is disposed in the coupling pin of the coupling device, which serves to supply media to the instrument and is accessible from the lateral surface of the coupling pin or is disposed in the coupling pin base behind an annular step surface and is accessible from the annular step surface.

The restricted accessibility to the memory element has proven to be a disadvantage of these embodiments, in particular the arrangement of the memory element in the interior of the medical instrument, in particular in the sleeve wall surrounding the coupling recess, in the coupling pin itself or in the coupling pin base. With these known arrangements, the memory element is accessible from one side or from at most two sides. Thus data and/or energy can be transferred to the memory element and from the latter to a transmission unit only to a limited extent.

In the medical, in particular dental, field, it is also common to fabricate the outer sleeves of the instruments as well as the two coupling elements of the coupling devices, in particular the sleeves of the recesses as well as the coupling pins from a metallic material. In the case of inductive energy and/or data transfer between a memory and a reading device, it is necessary for all the parts disposed between the two elements to be made of a material that is not electrically conductive, so as not to endanger the energy and data transfer by opposing fields generated in the electrically conductive parts. Thus, with the arrangement of the memory element in the interior of the instrument, as is known in the state of the art, there is the risk that opposing fields, which would endanger an inductive energy transfer and/or data transfer between the memory and the reading device, might be generated by electrically conductive parts, in particular metallic parts such as the outer sleeve, for example, the sleeve for the coupling recess, the coupling pin or the shafts themselves mounted therein.

Another disadvantage of the embodiments known in the state of the art is the lack of a possibility for designing existing coupling elements, in particular medical instruments, for sending and/or receiving data and/or energy. Because the memory element is disposed in the interior of the instrument, in particular in the coupling sleeve forming the recess, it is possible to retrofit existing instruments with a memory element only with great expense and effort or not at all.

SUMMARY

Therefore, the object of the present invention is to create a coupling device for detachably connecting a medical, in particular dental, instrument to a drive unit or a supply hose which will make it possible in particular to safely and reliably transfer data and/or energy from the one coupling element to the other coupling element of the coupling device and also to design existing coupling elements, in particular medical instruments, for sending and/or receiving data and/or energy.

According to one exemplary embodiment of a coupling device for detachably connecting a medical, in particular dental, instrument to a drive unit or a supply hose for transfer of data and/or energy and optionally a drive movement and/or a working medium, in particular a fluid between the drive unit or the supply hose and the instrument, the coupling device comprises a first and second coupling element, wherein one of the two coupling elements being designed as a coupling recess, into which a coupling protrusion of the other coupling element can be inserted, wherein a positioning element is disposed on one of the two coupling elements, this positioning element being insertable into an indentation on the other coupling element to position the two coupling elements in a defined angular position about their shared axis to one another, and wherein one of the two elements, the positioning element or the indentation, has a memory unit for storage of data, preferably instrument-related data, and the other of the two elements has a transfer unit, so that data from the memory unit of the one coupling element can be transferred by means of the transfer unit to the other coupling element of the coupling device.

According to a first exemplary embodiment of the coupling device, the positioning element of the one coupling element has the memory unit, such that for transfer of the data, in particular instrument-related data, to the other coupling element, the positioning element has at least one electric contact connected to the memory unit and connectable to an electric contact of the other coupling element, in particular the transfer unit, which is disposed in the recess for accommodating the positioning element, so that the data and/or energy can be transferred between the two coupling elements in a hardwired process. The at least one electric contact of the memory unit is therefore in particular disposed in the end surface of the positioning element, and the at least one electric contact of the transfer unit is disposed in a base surface of the indentation and is thus accessible for the other contact.

The positioning element itself is preferably fabricated from a material which is not magnetically conductive and is not electrically conductive, in particular it is made of a plastic, glass or ceramic and is supported moveable on the one coupling element of the coupling device, so that it is displaceable essentially in parallel with the axis of rotation of the coupling device. In addition, the element is preferably designed to be releasable from the coupling element, so that it can be replaced.

The memory unit itself preferably comprises an electronically programmable memory, which is designed either as a readable memory or as a readable and writable memory. The transfer unit is preferably formed by a receiving unit having a reader for processing and/or for workup of the transmitted data.

According to a second exemplary embodiment of the coupling device, the positioning element with the memory unit of the one coupling element has a reading and/or writing device, in particular a first coil, wherein a second coil for data and/or energy transfer is disposed in the indentation of the other coupling element. The two coils are therefore mounted on one or more side walls of the positioning element or the indentation, on the end surface of the positioning element or on the base surface of the indentation.

The at least one first coil of the memory unit as well as the memory element are preferably disposed one above the other, or alternatively, are disposed side by side on a shared carrier circuit board, in a separate housing, and together form an RFID unit, which is in turn accommodated in the positioning element, preferably by means of an injection-molding process.

The coils of the memory unit and the transfer unit are preferably surrounded by a soft magnetic material, in particular ferrite, nickel-zinc or manganese-zinc for conducting and/or aligning the field lines of the magnetic field in the direction of the first or second coil and/or being made of an electrically nonconductive material, in particular a plastic, silicone, resin, ceramic, adhesive, lacquer or glass to prevent a weakening of the magnetic field due to self-generated and/or received foreign fields.

According to a third exemplary embodiment of the coupling device, in addition to having the memory unit for storage of data and the transfer unit, the first and second coupling elements also have electrical contacts and/or reading and/or writing devices for hardwired and/or wireless transmission of data, signals and/or energy from the one coupling element to the other coupling element of the coupling device.

According to all the exemplary embodiments described above, the positioning element and the indentation are designed for rotationally fixed connection of the two coupling elements of the coupling device. In particular when the positioning element and the indentation engage with one another, no twisting of either coupling element about its shared axis of rotation is possible.

The present coupling device is characterized by the following advantages.

The coupling device according to the invention permits reliable transfer of data and/or energy from the one coupling element to the other coupling element of the coupling device. Due to the arrangement of the memory unit for storage of preferably instrument-related data in the positioning element of the coupling device, the memory unit is disposed outside of the metallic parts of the coupling device, in particular outside of the outer sleeve of the instrument connected to the coupling element, the sleeve for the coupling recess, the coupling pin and the shafts mounted therein. This eliminates the danger of creating opposing fields in an inductive energy transfer and/or data transfer between a memory and a reading device.

Due to the preferred arrangement of the transmission unit in an indentation on the other coupling element of the coupling device, the transmission unit is mechanically protected from foreign influences.

Furthermore, the memory unit is accessible and/or readable and/or writable for the transfer unit from several sides. This also permits reliable data and energy transfer.

Another advantage of the invention is the possibility of designing pre-existing coupling elements, in particular medical instruments, for sending and/or receiving data and/or energy. Due to the fact that the positioning elements are designed to be releasable on existing medical instruments, it is possible to retrofit them with positioning elements, each having a memory unit with data, in particular instrument-related data. Despite the retrofitting, the instruments and/or coupling elements still remain compatible with the existing drive units and/or with their coupling elements without any functional restriction.

Within the scope of the invention, it is self-evident that the coupling device described above is not limited to use with a medical, in particular dental, instrument and a drive unit. Instead, the coupling device may be used for detachably connecting two medical, in particular dental, devices. Preferably at least one of the medical, in particular dental, devices is designed as a cleaning and/or care device, as a drive unit, a supply hose or an instrument having a drive device for a tool.

The invention is explained in greater detail below on the basis of multiple exemplary embodiments and in conjunction with the accompanying drawings.

BRIEF DESCRIPTION OF THE DRAWINGS

FIG. 1A and FIG. 1B show a first exemplary embodiment of the coupling device having a first coupling element on a medical, in particular dental, instrument and a second coupling element on a drive unit, respectively;

FIG. 2 shows a sectional diagram of the first exemplary embodiment of the coupling device from FIGS. 1A and 1B, with a memory unit having a memory element and an electric contact in the positioning element of the one coupling element and another electric contact as a transfer unit in the indentation to receive the positioning element in the other coupling element, in a partially installed state of the two coupling elements;

DETAILED DESCRIPTION

Figure 3:
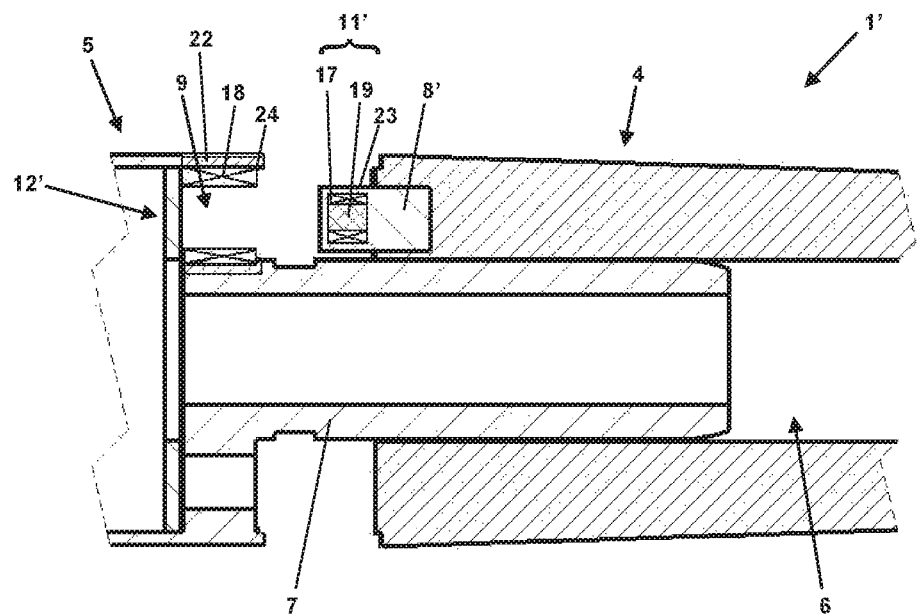
FIG. 3 shows a second exemplary embodiment of the coupling device, also in a sectional diagram, having a reading and/or writing device, in particular a first and second coil in the positioning element and in the indentation of the first and second coupling elements.

FIGS. 1A and 1B show a coupling device 1 for detachably connecting a medical, in particular dental, instrument 2 (e.g., a handpiece or handle) to a drive unit 3 for transfer of data and/or energy, a drive movement and a working medium, in particular a fluid, between the drive unit 3 and the instrument 2. The coupling device 1 therefore has a first coupling element 4 in the form of a coupling recess 6 on the medical instrument 2 and a second coupling element 5, which is designed as a coupling protrusion 7 on the drive unit 3.

To position the two coupling elements 4, 5 in relation to one another in a defined angular position about their common axis 10 about which they can rotate freely up to a coupled state of the two coupling elements 4, 5 to align a media line 31 of the drive unit 3, in particular for light or at least one fluid, to the corresponding media line 32 on the medical instrument 2, the coupling device 1, in particular the first coupling element 4 with the coupling recess 6 on the instrument 2, has a positioning element 8, which preferably extends from the coupling surface of the first coupling element 4 in the opposite direction to the coupling recess 6. The positioning element 8 is preferably designed as a lug, a continuation or protrusion and can be inserted into an indentation 9 on the other coupling element 5. The positioning element 8 and the indentation 9 are designed in particular for a rotationally fixed connection of the two coupling elements 4, 5.

For identification of the medical instrument 2 to supply the working media automatically depending on the instrument 2, which is connected via the drive unit 3 to a dental unit, the positioning element 8 of the first coupling element 4 has a memory unit for storage of data, preferably instrument-related data. In addition to the memory unit, at least one electric contact 13 is disposed in or on the element 8 in this exemplary embodiment, this contact being connectable to an electric contact 14 of a transmission unit 12 in the indentation 9 on the other coupling element 5 so that the data, in particular instrument-related data, can be transferred in a hardwired operation.

FIG. 2 shows the coupling device 1 from FIGS. 1A and 1B in a sectional diagram in a partially connected state of the two coupling elements 4, 5, where the coupling protrusion 7 on the second coupling element 5 is accommodated in the coupling recess 6 on the first coupling element 4, preferably the dental instrument 2. The positioning element 8 with the memory unit 11 of the first coupling element 4 is at least partially supported in a recess in the sleeve-shaped coupling part 33, in particular displaceably, and is prestressed by means of a spring 32 in relation to the indentation 9 on the other coupling part 5. The memory element 19 and the electric contact 14 of the memory unit 11 itself however are disposed outside of the sleeve-shaped coupling part 33 in the positioning element 8, so that these are accessible for the other coupling element 5 from several sides. The housing 27 of the positioning element 8, in particular the region surrounding the memory unit 11 is preferably made of a magnetically nonconductive and electrically nonconductive material, in particular a plastic, glass or ceramic.

The transfer of data and/or energy between memory unit 11, in particular between its memory element 19 and the transfer unit 12 which is preferably disposed in the indentation 9 of the other coupling element 5 takes place in a hardwired operation in this exemplary embodiment. The electric contacts 13, 14 are each mounted on the end surface 15 of the positioning element 8 and on the base surface 16 of the indentation 9 and/or are accessible for the corresponding contact 13, 14.

The electric contact 13 in the indentation 9 for receiving the positioning element 8 is preferably disposed on a carrier circuit board 22. The circuit board 22 itself is preferably designed in a ring shape with the coupling protrusion 7 extending through its central opening. In addition to the reading and/or writing device, in particular the electric contact 13, other electronic components may also be disposed on the circuit board 22, in particular those for data and/or energy transfer. A light source, in particular a light-emitting diode, is preferably soldered on the circuit board 22, with the media line 31 being designed as a window of the diode to transfer light from the drive unit 3 to the instrument 2. The electronic components, the transfer unit 12 and the circuit board 22 are preferably accommodated in a magnetically nonconductive and electrically nonconductive material, in particular plastic, glass or ceramic. This encapsulated unit encloses the coupling protrusion 7, which extends from the coupling base through the ring-shaped unit.

FIG. 3 shows a second exemplary embodiment of the coupling device 1', also in a sectional diagram, with a reading and/or writing device in the first and second coupling elements 4, 5, in particular with a first coil 17 in the positioning element 8' and a second coil 18 in the indentation 9. The positioning element 8' in this example is fixedly connected to the sleeve-shaped coupling part that surrounds the coupling recess 6. However, it is of course also possible with this exemplary embodiment as well as with all additional exemplary embodiments to prestress the positioning element 8' by means of a spring in relation to the indentation 9 on the other coupling part 5. Here again, the memory unit 11' and the memory element 19 and the coil 17 are disposed outside of the sleeve-shaped coupling part in the positioning element 8' of the first coupling element 4. The coil 17 is preferably disposed on the memory element 19, in particular between the memory element 19 and the lateral surface 23 of the positioning element 8'. The coil 18 of the transfer unit 12' of the other coupling element 5 with the coupling protrusion 7 is applied to a carrier circuit board 22, which is preferably designed at least partially to be sleeve-shaped and is disposed in the lateral surface 24 of the indentation 9. The two coils 17, 18 are thus disposed one inside the other for inductive coupling in the installed state of the coupling device 1'. This inductive coupling serves to supply energy to the memory unit 11' as well as serving the purpose of exchanging data. The data exchange takes place between the two coils 17, 18 in the high-frequency range or in the radio frequency range, where the memory unit 11' is designed as an MD unit, in particular as an RFID label or a transponder consisting of an RFID chip and a coil 17.

Figure 4:
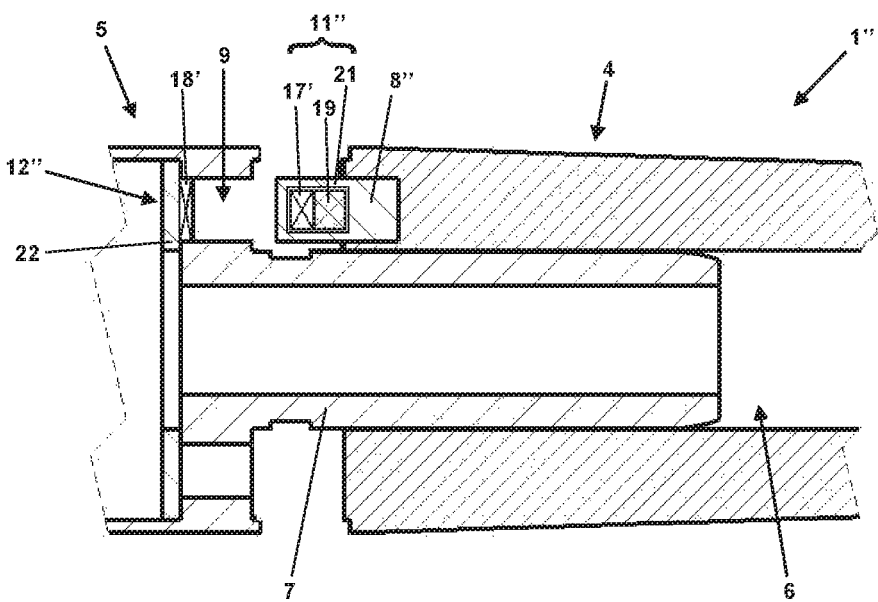
FIG. 4 shows a third exemplary embodiment of the coupling device having a first coil and a memory element disposed in its own housing in the positioning element.

FIG. 4 shows a third exemplary embodiment of the coupling device 1" with a first and second coupling element 4, 5 having a memory unit 11" with a first coil 17' and a memory element 19 which are disposed in a shared housing 21 in the positioning element 8"'. The housing 21 as well as the components disposed therein, in particular the memory 19 and coil 17', together for an RFID unit, which is accommodated in the positioning element 8", preferably by means of an injection-molding process.

Alternatively, the memory 19 and the coil 17' may be disposed in a housing 21 made of glass, plastic, ceramic or metal. The coil 18' of the transfer unit 12" is disposed on a carrier circuit board 22 in the region of the base surface of the indentation 9 to receive the positioning element 8". The two coils 17', 18' are thus disposed directly side by side or opposite one another in a coupled state of the two coupling elements 4, 5, in particular in an arrangement of the coupling protrusion 7 in the coupling recess 6. Particularly reliable data exchange and/or energy exchange is/are achieved in this way.

Figure 5:
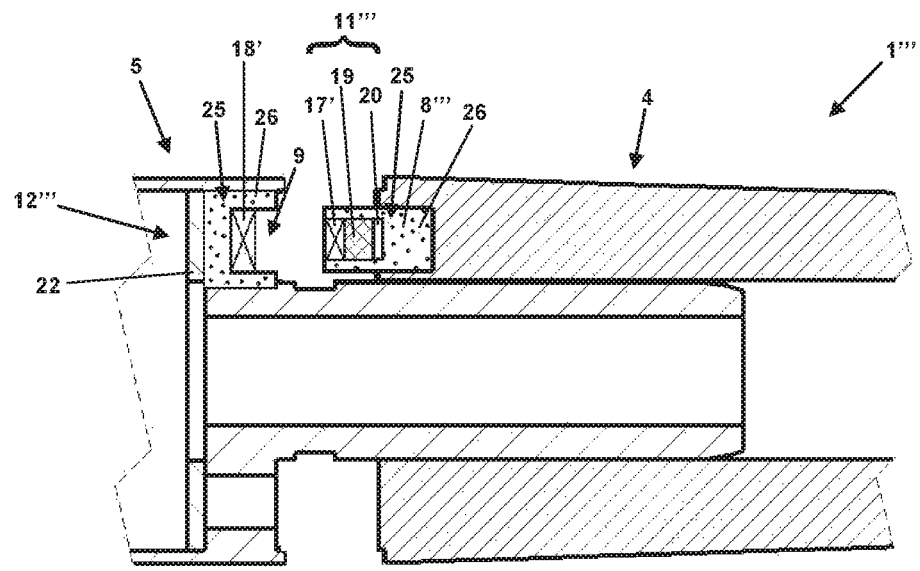
FIG. 5 shows a fourth exemplary embodiment of the coupling device, where the first and second coils of the two coupling elements are surrounded by a soft magnetic material and a material that is not electrically conductive.

FIG. 5 shows a fourth exemplary embodiment of the coupling device 1''', wherein the first and second coils 17', 18' of the two coupling elements 4, 5 are surrounded by a soft magnetic material 25 and an electrically nonconductive material 26. The coil 17' in the positioning element 8" is positioned on the memory element 19, which is in turn disposed on a carrier circuit board 20. The carrier circuit board 20 preferably comprises an electrically insulating material, for example, plastic, glass or ceramic. The coil 18' of the transfer unit 12''' of the other coupling element 5 is also disposed on such a carrier circuit board 22. To permit a particularly good and interference-free energy transfer and data transfer, according to a preferred exemplary embodiment, the coil 18' of the transfer unit 12''' disposed in the indentation 9 and also the memory unit 11''' in the positioning element 8''' are surrounded by a soft magnetic material 25, in particular ferrite, nickel-zinc or manganese-zinc for conducting and/or aligning the field lines of the magnetic field in the direction of the first or second coil 17, 18' and/or surrounded by an electrically nonconductive material 26, in particular plastic, silicone, resin, ceramic, adhesive, lacquer or glass to prevent weakening of the magnetic field due to self-generated and/or received foreign fields. The electrically nonconductive material 26 preferably encloses the coil 18' and the memory unit 11''' on all sides. In this exemplary embodiment, the two components 18', 11''' have both materials 25, 26 on at least three sides, wherein the soft magnetic material 25 is designed here in particulate form and each is embedded in the other material 26.

Figure 6:
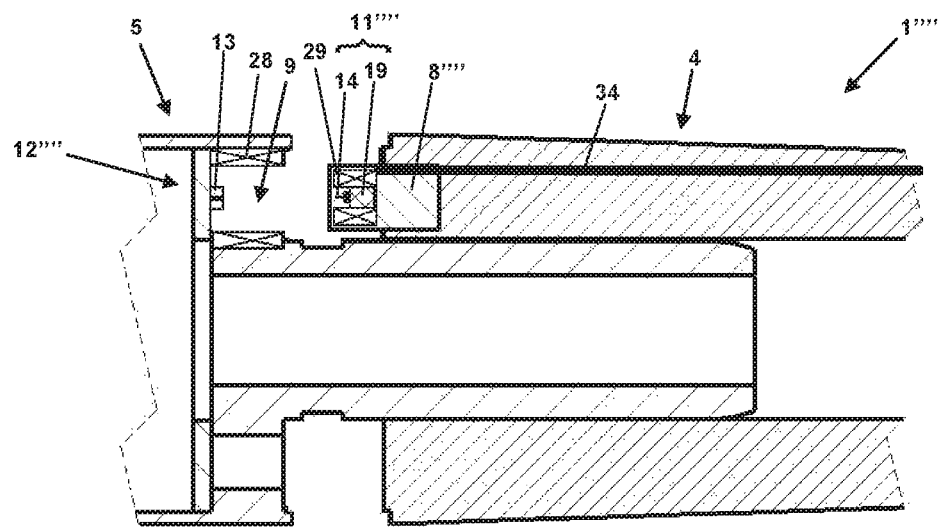
FIG. 6 shows a fifth exemplary embodiment of the coupling device, wherein the coupling elements each have an additional reading and/or writing device for wireless transmission of data, signals and/or energy from the one coupling element to the other coupling element.

FIG. 6 shows a fifth exemplary embodiment of the coupling device 1" where the coupling elements 4, 5 each have another reading and/or writing device 28, 29 for wireless transfer of data, signals and/or energy from one coupling element to the other coupling element. The reading and/or writing device 28, 29 here is also disposed in the positioning element 8"" and in the indentation 9 of the transfer unit 12"", next to the electric contacts 13, 14 for data and/or energy exchange between the memory element 19 of the memory unit 11"" and the transfer unit 12"".

As already shown in FIGS. 1A, 1B and 2, the electric contacts 13, 14 are each mounted on end surface of the positioning element 8"" and on the base surface of the indentation 9 and are accessible for the corresponding contact 13, 14. The coils 28, 29 for additional transfer of data, signals and/or energy are preferably disposed one inside the other in an installed state of the coupling device 1"". To do so, the coil 29 is preferably disposed between the memory element 19 and the lateral surface of the positioning element 8"" and the coil 28 of the transfer unit 12"" of the other coupling element 5 is preferably disposed in the lateral surface of the indentation 9.

An electric line 34 preferably extends from the coil 29 to an electronic component in the medical, in particular dental, instrument, which is preferably connected to the coupling element 4. The coils 28, 29 here serve the purpose of energy transfer, preferably for a light source in the instrument and/or for transfer of data, in particular of measured data such as, for example, sensor data for torques, temperatures and/or for transfer of signals such as, for example, root canal positioning signals from the electronic component such as, for example, a sensor or an evaluation unit to a dental unit.

The present invention is not limited to the exemplary embodiments described here but instead includes all embodiments which apply and contain the principle logical function principle of the invention. In addition, all the features of all the exemplary embodiments described and depicted here may be combined with one another.

What is claimed is:

1. A coupling device for detachably connecting a medical or dental handpiece to a drive unit or a supply hose for transfer of at least one of data and energy between the drive unit or the supply hose and the handpiece, comprising:

a first coupling element provided on an end of the handpiece facing the drive unit or supply hose when the handpiece and the drive unit or supply hose are coupled together and a second coupling element provided on an end of the drive unit or supply hose facing the handpiece when the handpiece and the drive unit or supply hose are coupled together, wherein one of the first and second coupling elements comprises a coupling recess and the other of the first and second coupling elements comprises a coupling protrusion insertable into the coupling recess, and wherein one of the first and second coupling elements comprises a positioning element and the other of the first and second coupling elements comprises an indentation into which the positioning element can be inserted to position the coupling elements in a defined angular position about a shared axis relative to one another, wherein one of the first and second coupling elements comprises an electronically programmable memory for storage of data having an REED chip and a first coil and the other of the first and second coupling elements comprises a second coil that is part of a transfer unit, so that data can be inductively transferred from the electronically programmable memory of the one coupling element to the other coupling element by the first coil and the second coil, and wherein the positioning element comprises a lug or protrusion forming a housing with a plurality of walls forming an accommodation, wherein the first coil is received and injection molded within the accommodation of the lug or protrusion, and wherein the lug or protrusion extends from a coupling surface of one of the first or second coupling elements such that at least a portion of the lug or protrusion and at least a portion of the first coil accommodated within the housing of the lug or protrusion are arranged to protrude axially beyond an outer sleeve of the respective first or second coupling element for inductive data transfer to and from the electronically programmable memory and are insertable in the indentation.

2. The coupling device according to claim 1, wherein the electronically programmable memory is entirely housed within the accommodation of the lug or protrusion.

3. The coupling device according to claim 2, wherein the electronically programmable memory is injection molded in the accommodation of the lug or protrusion.

4. The coupling device according to claim 1, wherein the at least one first coil and the electronically programmable memory are disposed adjacent each other on a shared carrier circuit board in the positioning element.

5. The coupling device according to claim 4, wherein the housing of the positioning element is a shared housing for the first coil and the electronically programmable memory.

6. The coupling device according to claim 1, wherein the first coil is disposed in or on at least one side wall or end surface of the positioning element, so that the first coil of the positioning element can be coupled to the second coil.

7. The coupling device according to claim 1, wherein the second coil is disposed adjacent the indentation for the positioning element on at least one of the side walls or base surface of the indentation, so that the second coil of the transfer unit can be coupled to the first coil of the electronically programmable memory.

8. The coupling device according to claim 1, wherein the first coil and second coil are surrounded by soft magnetic material for conducting and/or aligning the field lines of the magnetic field.

9. The coupling device according to claim 8, wherein the soft magnetic material comprises at least one of ferrite, nickel-zinc or manganese-zinc.

10. The coupling device of claim 1, wherein the first coil and the second coil are surrounded by electrically nonconductive material to prevent weakening of the magnetic field due to self-generated and/or received foreign fields.

11. The coupling device according to claim 10, wherein the electrically nonconductive material comprises at least one of plastic, silicone, resin, ceramic, adhesive, lacquer or glass.

12. The coupling device according to claim 1, wherein the housing of the positioning element is made of a magnetically nonconductive and electrically nonconductive material at least in a region surrounding the first coil.

13. The coupling device according to claim 1, wherein the positioning element comprises a spring mount, so that the lug or protrusion of the positioning element and the first coil received therein can be displaced substantially in parallel with an axis of rotation of the respective first or second coupling element.

14. The coupling device according to claim 1, wherein the positioning element is configured to be releasable from the first or second coupling element into which the positioning element is insertable.

15. The coupling device according to claim 1, wherein the positioning element and the transfer unit have additional electric contacts and/or reading and/or writing devices for hardwired and/or wireless transfer of data, signals and/or energy between the first and second coupling elements.

16. A method of using the coupling device according to claim 1 for detachably connecting the handpiece with the first coupling unit to a drive unit or supply hose having the second coupling unit.

17. The coupling device of claim 1, further comprising the medical or dental handpiece for transfer of at least one of data or energy, and the drive unit or the supply hose, the first and second coupling elements being positioned at respective ends thereof to couple together the medical or dental handpiece and the drive unit or supply hose.

18. The coupling device of claim 1, further comprising a first dental device and a second dental device, the first and second coupling elements being positioned at respective ends thereof to couple together the first dental device and the second dental device.

19. A coupling device for detachably connecting a medical or dental handpiece to a drive unit or a supply hose for transfer of at least one of data and energy between the drive unit or the supply hose and the handpiece, comprising:

a first coupling element provided on an end of the handpiece facing the drive unit or supply hose when the handpiece and the drive unit or supply hose are coupled together and a second coupling element provided on an end of the drive unit or supply hose facing the handpiece when the handpiece and the drive unit or supply hose are coupled together, wherein one of the first and second coupling elements comprises a coupling recess and the other of the first and second coupling elements comprises a coupling protrusion insert into the coupling recess, wherein one of the first and second coupling elements comprises a positioning element and the other of the first and second coupling elements comprises an indentation into which the positioning element can be inserted to position the coupling elements in a defined angular position about a shared axis relative to one another, wherein one of the first and second coupling elements comprises an RFID transponder having an RFID chip and a first coil coupled to the REED chip, wherein the first coil and the RFID chip are disposed in a shared housing, wherein the other of the first and second coupling elements comprises a second coil that is a part of a transfer unit, and wherein data can be inductively transferred from the MD transponder of the one coupling element to the other coupling element by the first coil and the second coil, and wherein the positioning element comprises a lug or protrusion having a plurality of walls forming an accommodation, wherein the shared housing comprising the first coil and the RFID chip is received in the accommodation of the lug or protrusion, and wherein the lug or protrusion extends from a coupling surface of one of the first or second coupling elements such that at least a portion of the lug or protrusion and at least a portion of the first coil are arranged to protrude axially beyond an outer sleeve of the respective first or second coupling element for inductive data transfer from the RFID transponder and are insertable in the indentation.

20. The coupling device of claim 19, wherein the shared housing comprising the first coil and the RFID chip is injection molded in the accommodation of the lug or protrusion.

21. The coupling device according to claim 19, wherein the shared housing is made of a magnetically nonconductive and electrically nonconductive material at least in a region surrounding the first coil.

22. The coupling device according to claim 19, wherein the positioning element comprises a spring mount, so that the lug or protrusion of the positioning element can be displaced substantially in parallel with an axis of rotation of the respective first or second coupling element.

23. The coupling device of claim 19, further comprising the medical or dental handpiece for transfer of at least one of data or energy, and the drive unit or the supply hose, the first and second coupling elements being positioned at respective ends t :0 couple together the medical or dental handpiece and the drive unit or supply hose.

* * * * *

UNITED STATES PATENT AND TRADEMARK OFFICE
CERTIFICATE OF CORRECTION

PATENT NO. : 10,874,480 B2
APPLICATION NO. : 16/058968
DATED : December 29, 2020
INVENTOR(S) : Mangelberger et al.

Page 1 of 1

It is certified that error appears in the above-identified patent and that said Letters Patent is hereby corrected as shown below:

In the Claims

Column 12, Line 21, Claim 23, "ends t :0 couple" should read --ends thereof to couple--.

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*